(12) United States Patent
Song et al.

(10) Patent No.: US 11,798,658 B2
(45) Date of Patent: Oct. 24, 2023

(54) MULTI-SCALE METHOD FOR SIMULATING MECHANICAL BEHAVIORS OF MULTIPHASE COMPOSITE MATERIALS

(71) Applicant: BEIJING UNIVERSITY OF TECHNOLOGY, Beijing (CN)

(72) Inventors: Xiaoyan Song, Beijing (CN); Hao Lu, Beijing (CN); Yanan Li, Beijing (CN); Fawei Tang, Beijing (CN)

(73) Assignee: BEIJING UNIVERSITRY OF TECHNOLOGY, Beijing (CN)

(*) Notice: Subject to any disclaimer, the term of this patent is extended or adjusted under 35 U.S.C. 154(b) by 0 days.

(21) Appl. No.: 16/980,370

(22) PCT Filed: Oct. 16, 2019

(86) PCT No.: PCT/CN2019/111434
§ 371 (c)(1),
(2) Date: Sep. 11, 2020

(87) PCT Pub. No.: WO2020/237977
PCT Pub. Date: Dec. 3, 2020

(65) Prior Publication Data
US 2021/0118530 A1    Apr. 22, 2021

(30) Foreign Application Priority Data

May 27, 2019   (CN) .......................... 201910447052.6

(51) Int. Cl.
*G06F 30/23*    (2020.01)
*G16C 60/00*    (2019.01)
(Continued)

(52) U.S. Cl.
CPC ............. *G16C 60/00* (2019.02); *G06F 30/23* (2020.01); *G16C 10/00* (2019.02); *G16C 20/80* (2019.02);
(Continued)

(58) Field of Classification Search
CPC ........ G16C 60/00; G16C 10/00; G16C 20/80; G06F 30/23; G06F 2111/14; G06F 2113/26; G06F 2111/10
See application file for complete search history.

(56) References Cited

U.S. PATENT DOCUMENTS

2007/0185694 A1    8/2007  Rousselier et al.
2011/0166843 A1*   7/2011  Hsu .......................... G06F 30/20
                                                            703/10
(Continued)

FOREIGN PATENT DOCUMENTS

CN   102222142 A   10/2011
CN   106066913 A   11/2016
(Continued)

OTHER PUBLICATIONS

S. Hajilar, B. Shafei, "Nano-scale investigation of elastic properties of hydrated cement paste constituents using molecular dynamics simulations" pp. 216-226 (Year: 2015).*

(Continued)

*Primary Examiner* — Kibrom K Gebresilassie
(74) *Attorney, Agent, or Firm* — J.C. PATENTS

(57) ABSTRACT

A computer simulation analysis method suitable for describing the mechanical behavior of multiphase composites based on the real microstructure of materials relates to a multidisciplinary field such as computational material science, simulation and high throughput calculation. Through the first-principles calculation under nano scale, the molecular dynamics simulation under micro scale, and the thermodynamic calculation under mesoscopic scale, various physical parameters needed for the finite element simulation under macro scale can be obtained, including the elastic and plastic physical parameters of each phase in the composite at different temperature and different grain sizes. Focused ion beam experiment and image processing are adopted to (Continued)

Figure 1:
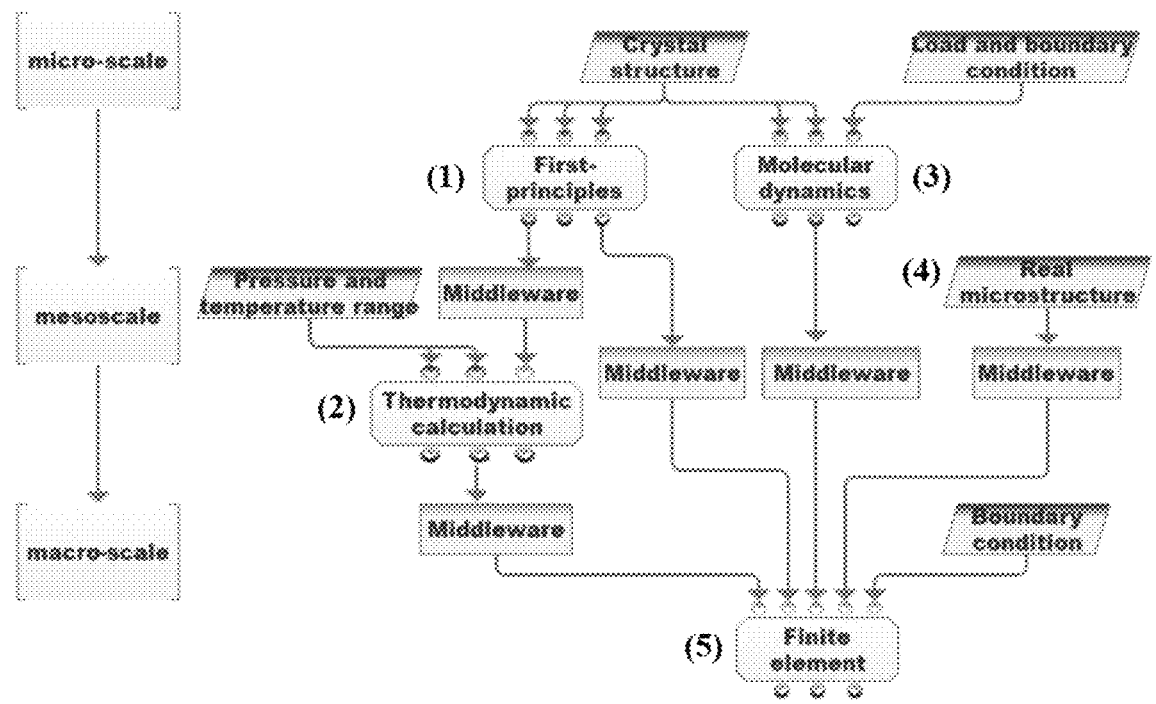

obtain real material microstructure. Through the parameter coupling and parameter transfer among the calculated results of various scales, combining the microstructure of the material, stress-strain relationship, stress distribution and its evolution law, plastic deformation and other mechanical behaviors of the multiphase composites under complex stress and different temperature can be simulated.

3 Claims, 3 Drawing Sheets

(51) Int. Cl.
 G16C 10/00 (2019.01)
 G16C 20/80 (2019.01)
 G06F 111/14 (2020.01)
 G06F 113/26 (2020.01)
 G06F 111/10 (2020.01)

(52) U.S. Cl.
 CPC ....... G06F 2111/10 (2020.01); G06F 2111/14 (2020.01); G06F 2113/26 (2020.01)

(56) References Cited

U.S. PATENT DOCUMENTS

2017/0096874 A1* 4/2017 Parsons .................. E21B 33/14
2018/0292465 A1* 10/2018 Osara .................. G01M 5/0033
2019/0384878 A1* 12/2019 Darcy ..................... G06F 30/23

FOREIGN PATENT DOCUMENTS

| CN | 107368642 A | 11/2017 |
| CN | 108664731 A | 10/2018 |
| CN | 108875260 A | 11/2018 |
| CN | 110210103 A | 9/2019 |
| EP | 3447717 A1 | 2/2019 |
| JP | 2012220417 | 11/2012 |

OTHER PUBLICATIONS

K. Boudia, M. Ameri, Y. Al-Douri, I. Ameri, H. Bouafia, Investigations of structural, elastic, electronic and thermodynamic properties of lutetium filled skutterudite LuFe4P12 under pressure effect: FP-LMTO method pp. 867-878 (Year: 2015).*
C. Toher, C. Oses J. J. Plata, . . . "Combining the Aflow Gibbs and elastic libraries to efficiently and robustly screen thermomechanical properties of solids" pp. 1-26 (Year: 2017).*
NPL1: "Comment on "The effect of temperature on the grain growth of nanocrystalline metals and its simulation by molecular dynamics method"", Computational Materials Science 56(2012) 185-187.
NPL2: "Deformation and plastic coordination in WC-Co composite—Molecular dynamics simulation of nanoindentation", Materials and Design 120(2017) 193-203.
NPL3: "Investigations on the Thermo-elastic, Hardness and Thermodynamic Properties of Rh3Ta Intermetallic Compound under Various Pressures and Temperatures", Natural Science Journal of Xiangtan University, vol. 40 No. 3 Jun. 2018.
NPL4: "Multiscale composite FEM modeling", Procedia Engineering 1(2009) 209-212.
NPL5: "Quantitative characterization of the microstructure and properties of nanocrystalline WC-Co bulk", Scripta Materialia 66(2012) 825-828.
NPL6: "Nanoscale stabilization of metastable phase: thermodynamic model and experimental studies", Acta Phys. Sin. Vol. 61, No. 20(2012).
NPL7: "Recrystallization in multi-phase materials containing particles with a two-class size distribution", Acta Metallurgiga Sinica vol. 40, No. 10, Oct. 2004, pp. 1009-1017.
NPL8: "Multiscale Materials Computational Methods", Science and Technology Reviews, 2015, 33(10).
First Office Action of the priority CN application 201910447052.6.
Notice of Allowance of the priority CN application 201910447052.6.
CN Search Report of the priority CN application 201910447052.6.
A1: "Research Progress in Multi-scale Mechanics of Composite Materials", Chinese Journal of Solid Mechanics, vol. 39, No. 1, Feb. 28, 2018, pp. 1-68.
A4: "Multiscale modeling of the mechanical properties of the carbon nanotube-reinforced composites", Master's thesis, Dalian University of Technology, published on Mar. 15, 2017.
International Search Report for PCT/CN2019/111434.
Written Opinion for PCT/CN2019/111434.

* cited by examiner

MULTI-SCALE METHOD FOR SIMULATING MECHANICAL BEHAVIORS OF MULTIPHASE COMPOSITE MATERIALS

CROSS-REFERENCE TO RELATED APPLICATION

This application is a national phase application of international application No. PCT/CN2019/111434 filed on Oct. 16, 2019 which claims the priority benefits of Chinese application No. 201910447052.6, filed on May 27, 2019. The contents of the above applications are hereby incorporated by reference in their entirety.

TECHNICAL FIELD

The present disclosure relates to a multidisciplinary field such as computational material science, simulation and high throughput calculation, especially relates to a computer simulation analysis method suitable for describing the mechanical behavior of multiphase composites based on the real microstructure of materials.

BACKGROUND ART

Based on the revolutionary thinking guided by materials genome program (MGI), computational materials science plays an increasingly important role in designing and development of new materials, which can provide accurate guidance for the design and development of new materials, effectively change the trial-and-error process of traditional material design and development, greatly improve the research and development efficiency of new materials, so as to effectively promote the development of high-performance new materials and the rapid development of related advanced manufacturing industry. At present, the commonly used methods of material calculation and simulation include, first-principles calculation and molecular dynamics simulation on the nano or micro scale, which can be used for screening the material composition and structure; the macroscopic finite element simulation and other methods can be used to calculate and analyze the service behavior and performance of materials. However, it is generally recognized that the input and output data and parameters of typical calculation models and algorithms used in the calculation and simulation methods at different scales are different.

Although there may be abundant methods and tools for the calculation at different scales, there is a serious lack of cross-scale and multi-scale calculation models and simulation methods. It is difficult to carry out data transmission among the calculation methods of different scales. Therefore, it is necessary to develop a multi-scale computing model for the intrinsic relationship between material composition, structure, process and performance, so as to realize the integrated design of material and the efficient and accurate prediction of material property and analysis.

Multiphase composites are widely used in engineering, and powder metallurgy is a typical way to prepare them. For the multiphase composite materials, due to the large difference in physical property parameters between the phases, especially the difference in thermal expansion coefficient will cause a large thermal residual stress in powder sintering process, and the residual thermal stress in prepared materials will have a great impact on material properties. Furthermore, the interaction between thermal stress and applied stress will greatly affect the mechanical behavior and performance of materials in service. The stress distribution is not homogenous in the multiphase composite materials, and different strain responses will appear in each phase during the process of service. Three-dimensional finite element simulation based on real microstructure of materials can reveal the heterogeneous strain response phenomenon accurately, which is of great significance to the study of mechanical behavior and properties of materials. However, three-dimensional finite element simulation requires a large number of material property parameters, and many parameters lack experimental data. Therefore, the multi-scale calculation model and algorithm are constructed, and the calculation methods of other scales are combined to provide parameter data for finite element simulation, which can solve the problem of data shortage in finite element simulation. Moreover, since the multi-scale model involves various nano, micro and macro scale calculation methods which can achieve the material composition screening, microstructure optimization and performance prediction at the same time, therefore, it is of great significance and application value to develop a multi-scale simulation method for the mechanical behavior of multiphase composites based on real material microstructure.

SUMMARY

The present invention provides a method for simulating the mechanical behavior of a multiphase composite at multiple scales based on the real microstructure of material. Through the first-principles calculation under nano scale, the molecular dynamics simulation under micro scale, and the thermodynamic calculation under mesoscopic scale, various physical parameters needed for the finite element simulation under macro scale can be obtained, including the elastic and plastic physical parameters of each phase in the composite at different temperatures and different grain sizes. Through the parameter coupling and parameter transfer among the calculated results of various scales, stress-strain relationship, stress distribution and its evolution law, plastic deformation and other mechanical behaviors of the multiphase composites under complex stress can be simulated.

To achieve the above purpose, the present disclosure provides a multi-scale simulation method for the mechanical behavior of multiphase composite materials, comprising the following technical schemes and steps:

(1) First-principles calculation under nano scale:

First-principles calculation under nano scale can respectively obtain the elastic properties of metal phase and ceramic phase of multiphase composite at 0K and the energy corresponding to the crystal structure of different volumes. The calculation scheme is as follows:

1.1 Calculating the Young's modulus, the bulk modulus, the shear modulus and the Poisson's ratio of metal and ceramic phases in the multiphase composites under the condition of 0K:

Firstly, the structural relaxation of single crystal structure of metal and ceramic phase materials is carried out respectively. The matrix element of the stiffness matrix, i.e., elastic constant C, is calculated by using the crystal structure after the relaxation.

$$\begin{pmatrix} \sigma_1 \\ \sigma_2 \\ \sigma_3 \\ \sigma_4 \\ \sigma_5 \\ \sigma_6 \end{pmatrix} = \begin{pmatrix} c_{11} & c_{12} & c_{13} & c_{14} & c_{15} & c_{16} \\ c_{21} & c_{22} & c_{23} & c_{24} & c_{25} & c_{26} \\ c_{31} & c_{32} & c_{33} & c_{34} & c_{35} & c_{36} \\ c_{14} & c_{24} & c_{34} & c_{44} & c_{45} & c_{46} \\ c_{15} & c_{25} & c_{35} & c_{45} & c_{55} & c_{56} \\ c_{16} & c_{26} & c_{36} & c_{46} & c_{56} & c_{66} \end{pmatrix} \begin{pmatrix} \varepsilon_1 \\ \varepsilon_2 \\ \varepsilon_3 \\ \varepsilon_4 \\ \varepsilon_5 \\ \varepsilon_6 \end{pmatrix} \quad (1)$$

Wherein $\sigma_i$ $\varepsilon_i$ $c_{ij}$ (i, j=1, 2, 3, 4, 5, 6) represent stress, strain and the elastic constants of single crystal materials respectively. Then the calculated elastic constants are converted into Young's modulus, bulk modulus, shear modulus and Poisson's ratio by using the Voigt-Reuss-Hill approximation.

$$B=(B_v+B_r)/2 \quad (2)$$

$$G=(G_v+G_r)/2 \quad (3)$$

$$E=9B\cdot G/(3\cdot B+G) \quad (4)$$

$$\upsilon=0.5\cdot(3B-2G)/(3B+G) \quad (5)$$

Wherein B represents the bulks modulus, G represents the shear modulus, E represents the Young's modulus and V represents the Poisson's ratio; Poisson's ratio is approximately unchanged with temperature; the bulks modulus, shear modulus and Young's modulus of the body will change with the change of temperature, its' calculation method is described in step (2). In formula (2) and (3), subscript v and r represent the approximate calculation methods of Voigt and Reuss respectively.

$$B_v=(c_{11}+c_{22}+c_{33})/9+2(c_{12}+c_{23}+c_{13})/9 \quad (6)$$

$$G_v=(c_{11}+c_{22}+c_{33}-c_{12}-c_{13}-c_{23})/15+(c_{44}+c_{55}+c_{66})/5 \quad (7)$$

$$B_r=1/(s_{11}+s_{22}+s_{33}+2s_{12}+2s_{13}+2s_{23}) \quad (8)$$

$$G_r=15/(4s_{11}+4s_{22}+4s_{33}-4s_{12}-4s_{13}-4s_{23}+3s_{44}+3s_{55}+3s6) \quad (9)$$

Wherein $S_{ij}$ (i, j=1, 2, 3, 4, 5, 6) represents the matrix element of compliance matrix, i.e., compliance coefficient S of the material. The compliance matrix S and the stiffness matrix C are inverse to each other.

1.2 Calculating the volume-energy relations of the metal and ceramic phases in the multiphase composites at 0K:

The cell volumes of the relaxed metal and ceramic phases in step 1.1 are respectively shrunk or expanded in the range of −10% to +10%, and the energies corresponding to different cell volumes are calculated.

(2) Thermodynamic calculation under mesoscopic scale:

The thermodynamic calculation under mesoscopic scale, based on the quasi-harmonic Debye model, can obtain the elastic properties and thermal expansion coefficients of metal phase and ceramic phase in the multiphase composite at different temperatures respectively. The calculation scheme is as follows:

2.1 Calculating the Young's modulus of metal and ceramic phase in multiphase composites at different temperatures:

non-equilibrium Gibbs free energy can be described as:

$$G^*=E(V)+pV+A_{vib}(\theta,T) \quad (10)$$

Wherein, E(V) represents the total energy of the cell calculated in step 1.2, P and V are external pressure and cell volume respectively, T represents temperature, $A_{vib}$ represents vibrational Helmholtz free energy, θ represents Debye temperature. Vibrational Helmholtz free energy $A_{vib}$ can be expressed as:

$$A_{vib}(\theta, T) = nk_BT\left[\frac{9}{8}\frac{\theta}{T} + 3\ln\left(1 - e^{-\theta/T}\right) - D(\theta/T)\right] \quad (11)$$

Wherein, D(θ/T) represents the Debye function, $$D(\theta/T) = \frac{3}{(\theta/T)^3}\int_0^{\theta/T} \frac{x^3}{e^x - 1}dx \ (x = \theta/T),$$

n represents the number of atoms in each cell, $k_B$ represents the Boltzmann constant, and the Debye temperature can be expressed as:

$$\theta = \frac{\hbar}{k_B}\left[6\pi^2 V^{1/2} n\right]^{1/3} f(\upsilon)\sqrt{\frac{B_s}{M}} \quad (12)$$

Wherein, M represents the cell mass, υ represents the Poisson's ratio, $\hbar$ represents the reduced Planck constant, and f(υ) represents the Poisson's ratio function $$f(\upsilon) = \left\{3\left[2\left(\frac{2}{3}\frac{1+\upsilon}{1-2\upsilon}\right)^{3/2} + \left(\frac{1}{3}\frac{1+\upsilon}{1-\upsilon}\right)^{3/2}\right]^{-1}\right\}^{1/3};$$

$B_s$ represents the adiabatic bulk modulus, which can be obtained by using the volume-energy relationship data obtained in step 1.2, the calculation method is as follows:

$$B_s = V\left(\frac{d^2E(V)}{dV^2}\right) \quad (13)$$

For a given (p,T), non-equilibrium Gibbs free energy minimizes the volume:

$$\left(\frac{\partial G^*}{\partial V}\right)_{p,T} = 0 \quad (14)$$

According to equation (14), the thermodynamic state of system can be obtained, that is, the universal equation of system state can be obtained, and the relationship between p, T and V of the system can be determined. Further, the bulk modulus of a certain temperature can be expressed as:

$$B_T = -V\left(\frac{\partial p}{\partial V}\right)_T \quad (15)$$

Temperature effect can be introduced into the bulk modulus by calculating formula (15), and the bulk modulus $B_T$ at a specific temperature can be obtained.

By formula (16):

$$E_T=3B_T(1-\upsilon) \quad (16)$$

The Young's modulus at different temperatures can be obtained. the Young's modulus $E_T$ at 0K calculated by formula (16) and the Young's modulus E at 0K calculated in step 1.1 has a difference $\Delta E=E_{T,0}-E$. This difference is used as the zero correction term of Young's modulus of other arbitrary temperatures calculated by formula (16), and the Young's modulus of any temperature is calculated accordingly $E(T)=E_T-\Delta E$;

Then the shear modulus G(T) at a particular temperature is calculated by $$G(T) = \frac{E(T)}{2(1+v)};$$

2.2 Calculating the thermal expansion coefficients of metal and ceramic phases at different temperatures:

On the other hand, heat capacity at constant pressure Cv and Gruneisen parameters γ can be described as:

$$C_V = 3nk_B \left[ 4D(\theta/T) - \frac{3\theta/T}{e^{\theta/T}-1} \right] \quad (17)$$

$$\gamma = -\frac{d \ln \theta}{d \ln V} \quad (18)$$

Based on formula (15), (17) and (18), the coefficient of thermal expansion α(T) can be obtained:

$$\alpha(T) = \frac{\gamma C_V}{B_T V} \quad (19)$$

Therefore, the temperature effect can be introduced into the coefficient of thermal expansion to calculate the coefficient of thermal expansion at different temperatures.

(3) Molecular dynamics simulation under micro scale:

Molecular dynamics simulation under micro scale can obtain the plastic properties of metal phase in the multiphase composites at a specific temperature (that is, different temperatures can be taken) and a specific grain size, plasticity of hard and brittle ceramic phase is negligible compared with that of metal phase.

Firstly, the single crystal model of metal phase in the multiphase composite is obtained by LAMMPS or other software, and then the polycrystalline model with different grain sizes (between 30 and 40 nm) within a relatively narrow range is constructed by Vironoi method in AtomEye or other software. Compression simulation is carried out for polycrystalline models with different grain sizes in a relatively narrow range at a specific temperature, and stress-strain curves are drawn. Yield strength and hardening coefficient can be read from the stress-strain curves. It is assumed that the hardening coefficient is independent of the grain size. In order to reduce the error, hardening coefficient of polycrystalline models of all grain sizes can be expressed as the average of hardening coefficient of several polycrystalline models with different small grain sizes.

For the yield strength $\sigma_s$ of any model with different grain size, it can be obtained by fitting the yield strength data of polycrystalline model in a relatively narrow range read from the stress-strain curve by using the Hall-Petch relation;

$$\sigma_s = \sigma_0 + kd^{-1/2} \quad (20)$$

Wherein, $\sigma_s$ represents the yield strength, $\sigma_0$ represents the lattice friction resistance when a single dislocation moves, k is a constant, and d represents the desirable arbitrary grain size;

In the fitting process, the calculation result of Peirls-Nabarro stress $\tau_p$ is adopted, $\sigma_0 \approx \tau_p$. The value of Peirls-Nabarro stress of the metal phase main slip system is used as Peirls-Nabarro stress, and the calculation formula is as follows:

$$\tau_p = \frac{2G(T)}{1-v} \exp\left[-\frac{2\pi a}{(1-v)b}\right] \quad (21)$$

Wherein, υ represents Poisson's ratio, and takes the calculated result in step 1.1; α represents plane spacing of the sliding plane, and b represents atomic spacing in the sliding direction, which can be calculated by using the relaxed crystal structure in step 1.1 through the geometric relationship. G(T) is the shear modulus at a specific temperature, and the calculated results in step 2.1 are taken.

(4) Building three-dimensional finite element model of real microstructure of multiphase composites:

Dual beam focused ion beam system is used to obtain composite materials cuboids with micron side length, for example, a cube with a side length of about 15 m is scanned at an interval of 20 nm. After image stack is obtained through the focused ion beam experiment, the image processing is carried out by Avizo or other software, the process is as follows:

First, the FIB Stack Wizard module in Avizo is applied to align and crop the image, as well as correct the shearing and shadow of the image, then median filter and edge-preserving smoothing Gaussian filter are used for denoising, finally, the image is binarized by threshold segmentation to distinguish the metal phase and ceramic phase. Therefore, composite microstructure images are obtained which can be used to construct geometric model in finite element model;

The process of constructing geometric model in finite element model of composite material structure is as follows:

(a) Extracting the coordinates of all pixels of metal phase in the above mentioned composite material microstructure images by using Matlab or other software, which is the pixel coordinates of the metal phase; (b) In the finite element software, geometric model in finite element model is established based on composite material microstructure images, which is the total geometric model in finite element model, it means both metal phase and ceramic phase are regarded as ceramic phase to establish geometric model; obtaining the coordinates of all elements in total geometric model; (c) according to the coordinates of all elements in total geometric model in (b) and the pixel coordinates of metal phase in step (a), the element that belongs to the metal phase in all elements of total geometric model is determined, and the material properties of such elements are modified to the material properties of metal phase to complete construction of the geometric model in finite element model of composite material microstructure;

(5) Simulating the mechanical behavior of multiphase composites by using finite element method:

Steps (1)-(3) are respectively calculated for the properties of independent or separate metal and ceramic phases in multiphase composites; according to the Poisson's ratio obtained from step (1), Young's modulus and thermal expansion coefficient of metal and ceramic phase at particular temperature obtained in step (2), yield strength and hardening coefficient of metal phase with particular grain size at specific temperature obtained in step (3), parameter model in finite element model of the ceramic and metal phase at different temperature is built; Reading the geometric model in finite element model of composite material structure constructed in step (4), and endowing the parameter model of ceramic phase and metal phase with different temperature to the geometric model of composite material microstructure, defining boundary conditions and constraints; applying load to geometric model in finite element model of composite material microstructure and calculating the complex stress; stress-strain relationship, stress distribution and its evolution, plastic deformation and other mechanical behaviors of the composite under different temperature and complex stress conditions are further quantitatively analyzed.

The advantages of the present disclosure are:
(1) The multiscale model and calculation method established by the present disclosure, with a unified combination of research objects and variables, closely connect and couple the models and methods of different scales to carry out the transmission and connection of multiple cross-scale data streams, so as to realize continuous calculation and simulation of nano-micro-mesoscopic-macroscale for the first time.
(2) The multi-scale model and calculation method established by the present disclosure can simultaneously realize the design and screening of material composition of multiphase system, the optimization of microstructure and the prediction of service performance.
(3) The establishment of the multi-scale calculation model and the introduction of real microstructure, temperature, pressure and other parameters of multi-phase composites can fully explain the mechanical behavior of multi-phase composites in service.
(4) The multi-scale continuous calculation and service process simulation are realized for the first time, which solves the common problem that traditional finite element method cannot accurately simulate the mechanical behavior of multi-phase composites due to serious lack of experimental data.
(5) The multi-scale model and calculation method established by the present disclosure can realize parallel high throughput calculation, can be popularized and applied to the calculation and simulation of multiple multi-phase complex material systems, thus opening up a new accurate and efficient way for the design and development of new high-performance materials.

BRIEF DESCRIPTION OF THE APPENDED DRAWINGS

Figure 2:
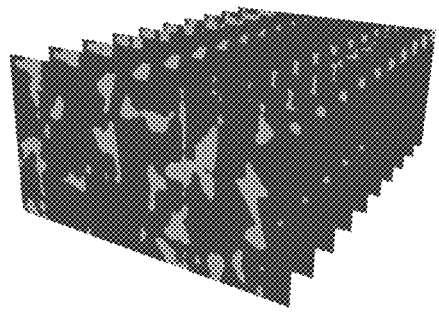
Figure 3:
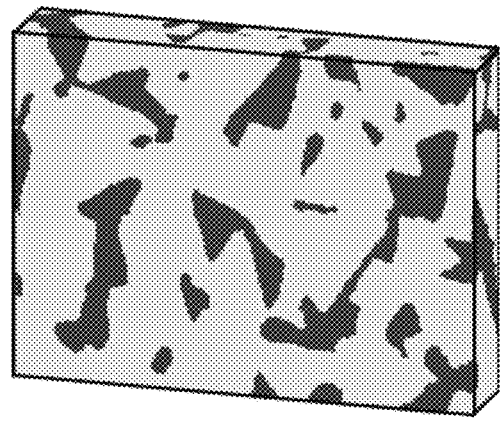
Figure 4:
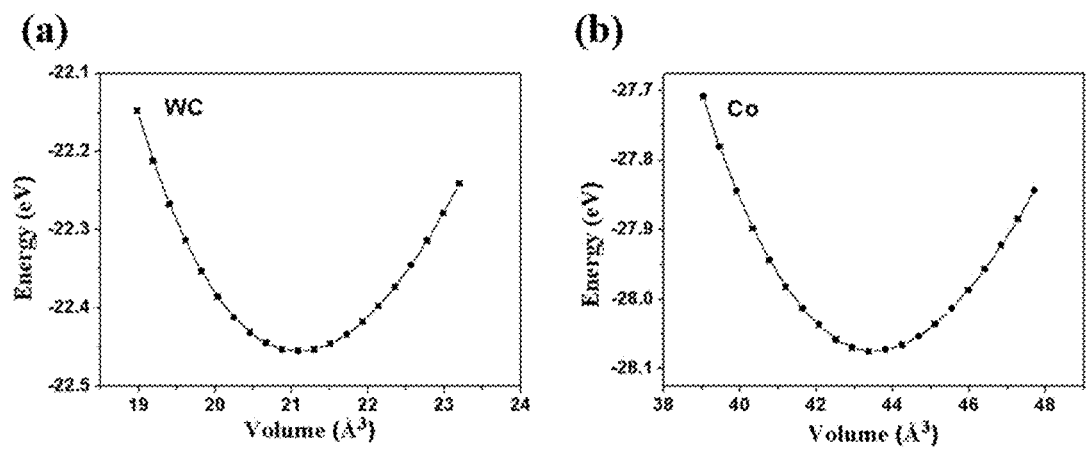
Figure 5:
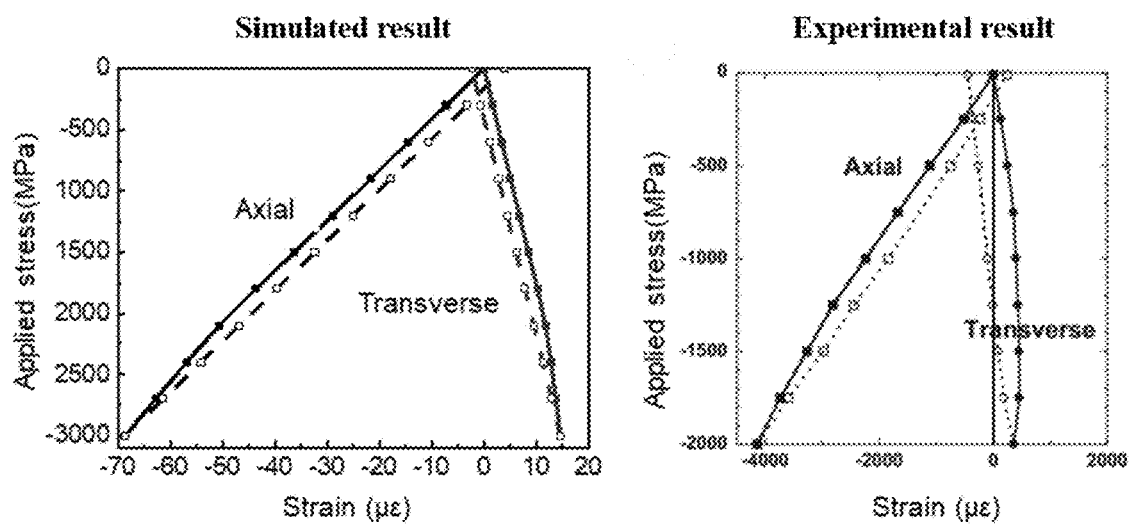
Figure 6:
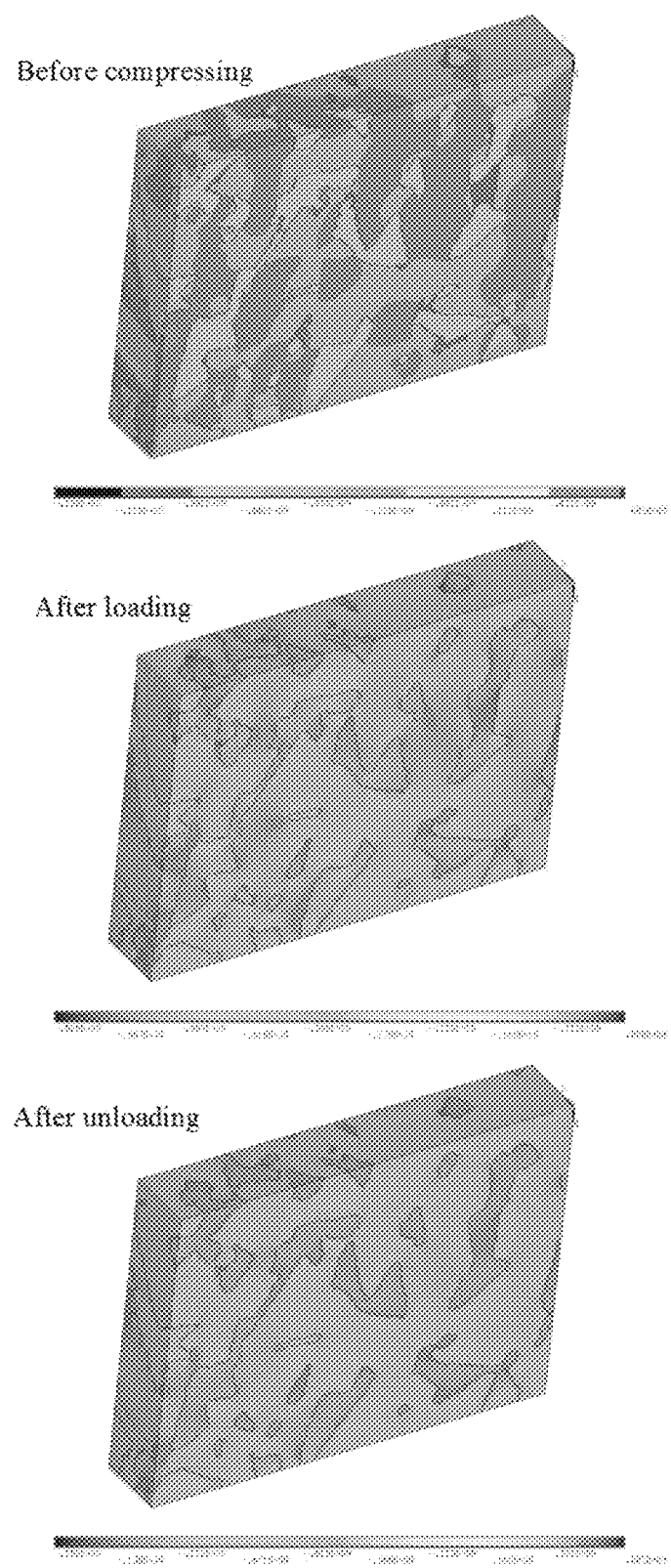

FIG. 1 is the flow chart of multi-scale simulation model and calculation method
FIG. 2 is an example of a binarization microstructure image used to construct a geometric model in finite element model
FIG. 3 shows the three-dimensional microstructure of a real material reproduced in the embodiment
FIG. 4 shows the volume-energy relationship calculated by the embodiment
FIG. 5 shows the comparison of stress-strain response curve of simulation results of the embodiment and experimental results
FIG. 6 is the simulation result of stress distribution in the embodiment

PREFERRED EMBODIMENT

The invention is further described in combination with embodiment, but the invention is not limited to the following embodiment. The following embodiments apply the multi-scale simulation calculation method of the present disclosure to study the stress-strain response and the distribution of stress and its evolution under the interaction between thermal stress and compression force for a composite material WC—Co.

Embodiment 1

As shown in FIG. 2, WC—Co image stack is obtained by focused ion beam experiment, and the images are binarized to obtain microstructure images which can be used to construct the geometric model in finite element. Three-dimensional finite element model of WC—Co with real microstructure is obtained by using Avizo software for image processing, the size of WC—Co finite element model is 1.77 μm (axial)×2.35 μm (horizontal)×0.40 μm (thick), which is shown in FIG. 3.

The Young's modulus, bulk modulus, shear modulus, Poisson's ratio and volume-energy relations of metal phase Co and ceramic phase WC in WC—Co composites at 0K are obtained by first-principles calculation. The volume-energy relationship is shown in FIG. 4.

|  | E (GPa) | B (GPa) | G (GPa) | υ |
|---|---|---|---|---|
| WC | 679.6 | 378.0 | 283.1 | 0.200 |
| Co | 276.1 | 205.6 | 108.2 | 0.276 |

By using the above Young's modulus, bulk modulus, shear modulus, Poisson's ratio and volume-energy relationship data at 0K which are calculated from the first principles, the Young's modulus after zero correction and thermal expansion coefficient of metal phase Co and ceramic phase WC at 300K, 700K and 1100K are obtained through thermodynamic calculation.

|  | Young's modulus E(T) (GPa) | | thermal expansion coefficient $\alpha(T)$ $(10^{-5}/K)$ | |
|---|---|---|---|---|
| WC | E(300) | 662 | α(300) | 0.58 |
|  | E(700) | 614 | α(700) | 0.74 |
|  | E(1100) | 560 | α(1100) | 0.82 |
| Co | E(300) | 261 | α(300) | 0.75 |
|  | E(700) | 220 | α(700) | 0.99 |
|  | E(1100) | 166 | α(1100) | 1.24 |

Three polycrystalline models of metal phase Co with grain sizes of 34 nm, 36 nm and 38 nm under uniaxial compression stress are simulated by means of molecular dynamics simulation under the conditions of 300K, 700K and 1100K to obtain the stress-strain curves. Values of yield strength and hardening coefficient are read from the stress-strain curves.

| Grain size of polycrystalline models (nm) | Temperature (K) | Yield strength (GPa) | Hardening coefficient (GPa) |
|---|---|---|---|
| 34 | 300 | 4.20 | 174.0 |
|  | 700 | 3.52 | 128.0 |
|  | 1100 | 2.93 | 126.4 |
| 36 | 300 | 3.53 | 162.0 |
|  | 700 | 3.43 | 134.8 |
|  | 1100 | 2.59 | 145.9 |
| 38 | 300 | 3.48 | 170.0 |
|  | 700 | 3.69 | 132.9 |
|  | 1100 | 2.69 | 145.3 |

The Peirls-Nabarro stress of metal phase Coat 300K, 700K and 1100K are calculated.

| Temperature (K) | Peirls-Nabarro stress (GPa) |
|---|---|
| 300 | 0.237 |
| 700 | 0.200 |
| 1100 | 0.151 |

Using the yield strength values read from stress-strain curves and the calculation results of Peirls-Nabarro stress, yield strength of metal phase Co with a grain size of 400 nm at 300K, 700K and 1100K is obtained by fitting the Hall-Petch relation. Assuming that the hardening coefficient of metal phase Co is independent of grain size, the hardening coefficient of metal phase Co at 400 nm is the average value of hardening coefficient calculated at 34 nm, 36 nm and 38 nm.

| Temperature (K) | Yield strength (GPa) | Hardening coefficient (GPa) |
|---|---|---|
| 300 | 1287 | 168.7 |
| 700 | 1204 | 131.9 |
| 1100 | 927 | 139.2 |

Poisson's ratio of metal phase Co and ceramic phase WC, and Young's modulus, thermal expansion coefficient, yield strength, hardening coefficient of Co at 300K, 700K, and 1100K, as well as Young's modulus and thermal expansion coefficient of WC at 300K, 700K, and 1100K are input into the parameter model in finite element model. The geometric model constructed by using real microstructure obtained by focusing ion beam experiment and image processing is read by finite element model. Using free boundary condition, the symmetrical boundary condition is set on three adjacent surfaces and free boundary condition is set on the other three opposite surfaces. The model is set from 1100K cooling down to 300K to simulate the cooling process after sintering. Stress-free state is set at 1100K, anelasto-plastic model with time variation is constructed. In the uniaxial compression simulation of sintered multiphase structure, the loading process is from 0 MPa to −3000 MPa, with an increase of 100 MPa for each load step, and the unloading process is from −3000 MPa to 0 MPa, with a decrease of 100 MPa for each load step.

The internal statistical stress-strain response of Co phase in compression process is calculated and compared with the test results of neutron diffraction method in the literature, which is shown in FIG. 5. The simulation results of this model show a similar trend to the stress-strain curves of the experimental results, which verifies the rationality of this model. On this basis, the stress-strain law, stress evolution law and plastic deformation behavior in compression process can be quantitatively characterized and analyzed based on real microstructure. FIG. 6 shows the distribution of stress before compression, after loading and after unloading. Then the relationship between microstructure-plastic deformation behavior-macroscopic properties is studied to provide reliable guidance for design and control of microstructure of multiphase materials.

The invention claimed is:
1. A multi-scale simulation method for mechanical behavior of a multiphase composite material, comprising the following steps:
(1) first-principles calculation under nano scale:
conducting first-principles calculation under nano scale to respectively obtain elastic properties of metal phase and ceramic phase of the multiphase composite material at temperature 0 K and an energy corresponding to a crystal structure of different volumes;
calculation scheme is as follows:
1.1 calculating Young's modulus, bulk modulus, shear modulus and Poisson's ratio of metal and ceramic phases of the multiphase composite material under temperature 0 K;
firstly, structural relaxation of a single crystal structure of metal and ceramic phase materials is carried out respectively; elastic constant C as matrix element of a stiffness matrix is calculated by using the crystal structure obtained after the structural relaxation;

$$\begin{pmatrix} \sigma_1 \\ \sigma_2 \\ \sigma_3 \\ \sigma_4 \\ \sigma_5 \\ \sigma_6 \end{pmatrix} = \begin{pmatrix} c_{11} & c_{12} & c_{13} & c_{14} & c_{15} & c_{16} \\ c_{12} & c_{22} & c_{23} & c_{24} & c_{25} & c_{26} \\ c_{13} & c_{23} & c_{33} & c_{34} & c_{35} & c_{36} \\ c_{14} & c_{24} & c_{34} & c_{44} & c_{45} & c_{46} \\ c_{15} & c_{25} & c_{35} & c_{45} & c_{55} & c_{56} \\ c_{16} & c_{26} & c_{36} & c_{46} & c_{56} & c_{66} \end{pmatrix} \begin{pmatrix} \varepsilon_1 \\ \varepsilon_2 \\ \varepsilon_3 \\ \varepsilon_4 \\ \varepsilon_5 \\ \varepsilon_6 \end{pmatrix} \quad (1)$$

wherein $\sigma_i$ $\varepsilon_i$ $c_{ij}$ (i,j=1,2,3,4,5,6) represent stress, strain and elastic constants of single crystal material respectively; then the calculated elastic constants are converted into Young's modulus, bulk modulus, shear modulus and Poisson's ratio by using Voigt-Reuss-Hill approximation;

$$B=(B_v+B_r)/2 \quad (2)$$

$$G=(G_v+G_r)/2 \quad (3)$$

$$E=9B \cdot G/(3 \cdot B+G) \quad (4)$$

$$\upsilon=0.5 \cdot (3B-2G)/(3B+G) \quad (5)$$

wherein B represents bulks modulus, G represents shear modulus, E represents Young's modulus and V represents Poisson's ratio; Poisson's ratio is approximately unchanged with temperature; the bulks modulus, the shear modulus and the Young's modulus will change with the change of temperature; in formula (2) and (3), subscript v and r represent the approximate calculation methods of Voigt and Reuss respectively;

$$B_v=(c_{11}+c_{22}+c_{33})/9+2(c_{12}+c_{23}+c_{13})/9 \quad (6)$$

$$G_v=(c_{11}+c_{22}+c_{33}-c_{12}-c_{13}-c_{23})/15+(c_{44}+c_{55}+c_{66})/5 \quad (7)$$

$$B_r=1/(s_{11}+s_{22}+s_{33}+2s_{12}+2s_{13}+2s_{23}) \quad (8)$$

$$G_r=15/(4s_{11}+4s_{22}+4s_{33}-4s_{12}-4s_{13}-4s_{23}+3s_{44}+3s_{55}+3s_{6}) \quad (9)$$

wherein $S_{ij}$ (i,j=1,2,3,4,5,6) represents matrix element of a compliance matrix S, which is compliance coefficient of the material; the compliance matrix S and a stiffness matrix C are inverse to each other;
1.2 calculating volume-energy relations of the metal and ceramic phases in the multiphase composite material at temperature 0 K;
the crystal structure obtained after structural relaxation of metal and ceramic phases in step 1.1 is shrunk or expanded in a range of −10% to +10%, and energies corresponding to different cell volumes are calculated;
(2) thermodynamic calculation of mesoscopic scale:
conducting thermodynamic calculation of mesoscopic scale, based on quasi-harmonic Debye model, to obtain elastic properties and thermal expansion coefficients of metal phase and ceramic phase in the multiphase composite material at different temperatures respectively; calculation scheme is as follows:

2.1 calculating the Young's modulus of metal and ceramic phase in the multiphase composite material at different temperatures:

non-equilibrium Gibbs free energy can be described as:

$$G^* = E(V) + pV + A_{vib}(\theta, T) \quad (10)$$

wherein, E(V) represents energies corresponding to the crystal structure with different volumes in step 1.2, P and V are external pressure and cell volume respectively, T represents temperature, $A_{vib}$ represents vibrational Helmholtz free energy, θ represents Debye temperature; vibrational Helmholtz free energy $A_{vib}$ can be expressed as:

$$A_{vib}(\theta, T) = nk_B T\left[\frac{9}{8}\frac{\theta}{T} + 3\ln(1 - e^{-\theta/T}) - D(\theta/T)\right] \quad (11)$$

wherein, D(θ/T) represents the Debye function, $$D(\theta/T) = \frac{3}{(\theta/T)^3}\int_0^{\theta/T} \frac{x^3}{e^x - 1} dx \; (x = \theta/T),$$

n represents the number of atoms in each cell, $k_n$ represents Boltzmann constant, and the Debye temperature can be expressed as:

$$\theta = \frac{\hbar}{k_B}\left[6\pi^2 V^{1/2} n\right]^{1/3} f(v)\sqrt{\frac{B_s}{M}} \quad (12)$$

wherein, M represents cell mass, v represents the Poisson's ratio, h represents reduced Planck constant, and f(v) represents the Poisson's ratio function $$f(v) = \left\{3\left[2\left(\frac{2}{3}\frac{1+v}{1-2v}\right)^{3/2} + \left(\frac{1}{3}\frac{1+v}{1-v}\right)^{3/2}\right]^{-1}\right\}^{1/3};$$

$B_s$ represents adiabatic elastic modulus, which can be obtained by using volume-energy relationship data obtained in step 1.2, a calculation method is as follows:

$$B_s = V\left(\frac{d^2 E(V)}{dV^2}\right) \quad (13)$$

for a given (p,T), non-equilibrium Gibbs free energy minimizes the volume:

$$\left(\frac{\partial G^*}{\partial V}\right)_{p,T} = 0 \quad (14)$$

according to equation (14), thermodynamic state of system can be obtained, an universal equation of system state can be obtained, and the relationship between p, T and V can be determined; further, the bulk modulus of a certain temperature can be expressed as:

$$B_T = -V\left(\frac{\partial p}{\partial V}\right)_T \quad (15)$$

temperature effect can be introduced into the bulk modulus by calculating formula (15), and the bulk modulus $B_T$ at a specific temperature can be obtained; by formula (16):

$$E_T = 3B_T(1-v) \quad (16)$$

the Young's modulus at different temperatures can be obtained; the Young's modulus $E_T$ at temperature 0 K calculated by formula (16) and the Young's modulus E at temperature 0 K calculated in step 1.1 has a difference $\Delta E = E_{T,0} - E$; this difference is used as the zero correction term of Young's modulus of other arbitrary temperatures calculated by formula (16), and the Young's modulus of any temperature is calculated accordingly $E(T) = E_T - \Delta E$;

then the shear modulus G(T) at a particular temperature is calculated by $$G(T) = \frac{E(T)}{2(1+v)};$$

2.2 calculating the thermal expansion coefficients of metal and ceramic phases at different temperatures:

heat capacity at constant pressure Cv and Gruneisen parameters γ can be described as:

$$C_V = 3nk_B\left[4D(\theta/T) - \frac{3\theta/T}{e^{\theta/T} - 1}\right] \quad (17)$$

$$\gamma = -\frac{d\ln\theta}{d\ln V} \quad (18)$$

based on formula (15), (17) and (18), the coefficient of thermal expansion α(T) can be obtained:

$$\alpha(T) = \frac{\gamma C_V}{B_T V} \quad (19)$$

therefore, the temperature effect can be introduced into the coefficient of thermal expansion to calculate the coefficient of thermal expansion at different temperatures;

(3) molecular dynamics simulation under micro scale:

molecular dynamics simulation under micro scale can obtain the plastic properties of metal phase in the multiphase composites at a specific temperature (that is, different temperatures can be taken) and a specific grain size, plasticity of hard and brittle ceramic phase is negligible compared with that of metal phase;

firstly, a single crystal model of metal phase in the multiphase composite is obtained, and then a polycrystalline model with different grain sizes within a relatively narrow range is constructed by Vironoi method; compression simulation is carried out for polycrystalline models with different grain sizes in a relatively narrow range at a specific temperature, and stress-strain curves are drawn; yield strength and hardening coefficient can be read from the stress-strain curves; it is assumed that the hardening coefficient is independent of grain size; in order to reduce the error, hardening coefficient of polycrystalline models of all grain sizes can be expressed as an average of hardening coefficient of several different small-grain sizes;

for the yield strength $\sigma_s$ of any model with different grain size, it can be obtained by fitting the yield strength data of polycrystalline model in a relatively narrow range read from the stress-strain curve by using the Hall-Petch relation;

$$\sigma_s = \sigma_0 + kd^{-1/2} \quad (20)$$

wherein, $\sigma_s$ represents the yield strength, $\sigma_0$ represents lattice friction resistance when a single dislocation moves, k is a constant, and d represents desirable arbitrary grain size; in the fitting process, a calculation result of Peirls-Nabarro stress $\tau_p$ is adopted, $\sigma_0 \approx \tau_p$;

a value of Peirls-Nabarro stress of the metal phase main slip system is used as the Peirls-Nabarro stress, and a calculation formula is as follows:

$$\tau_p = \frac{2G(T)}{1-v} \exp\left[-\frac{2\pi a}{(1-v)b}\right] \quad (21)$$

wherein, v represents Poisson's ratio, and takes the calculated result in step 1.1; a represents plane spacing of the sliding plane, and b represents atomic spacing in the sliding direction, which can be calculated by using the relaxed crystal structure in step 1.1 through the geometric relationship; G(T) is the shear modulus at a specific temperature, and calculated results in step 2.1 are taken;

(4) building three-dimensional finite element model of real microstructure of multiphase composites:

a dual beam focused ion beam system is used to obtain composite materials cuboids with micron side length; after image stack is obtained through focused ion beam experiment, an image processing is carried out, the image processing is as follows:

first, FIB Stack Wizard module is applied to align and crop the image, as well as correct the shearing and shadow of the image, then median filter and edge-preserving smoothing Gaussian filter are used for denoising, finally, the image is binarized by threshold segmentation to distinguish the metal phase and ceramic phase; therefore, composite microstructure images are obtained which can be used to construct a geometric model in finite element model; then constructing the geometric model;

(5) simulating the mechanical behavior of multiphase composites by using finite element method according to the Poisson's ratio obtained from step (1), Young's modulus and thermal expansion coefficient of metal and ceramic phase at particular temperature obtained in step (2), yield strength and hardening coefficient of metal phase with particular grain size at specific temperature obtained in step (3), a parameter model in finite element model of the ceramic and metal phase at different temperature is built;

reading the geometric model in finite element model of composite material structure constructed in step (4); endowing the parameter model of ceramic phase and metal phase with different temperature to the geometric model of composite material microstructure for calculation.

2. The multi-scale simulation method for the mechanical behavior of multiphase composite material in claim 1, comprising: in step (4), the process of constructing the geometric model in finite element model of composite material microstructure is as follows:

(a) extracting coordinates of all pixels of metal phase in a composite material microstructure image, which is the pixel coordinates of the metal phase; (b) in the finite element software, the geometric model in finite element model of the composite material microstructure image is established, which is a total geometric model in finite element model, it means both metal phase and ceramic phase are regarded as ceramic phase to establish the geometric model; obtaining coordinates of all elements in the total geometric model; (c) according to the coordinates of all elements in the total geometric model in (b) and the pixel coordinates of metal phase in step (a), an element that belongs to the metal phase in all elements of the total geometric model is determined, and material properties of such elements are modified to the material properties of metal phase to complete construction of the geometric model in finite element model of composite material microstructure.

3. The multi-scale simulation method for the mechanical behavior of multiphase composite material in claim 1, comprising: in step (5), defining boundary conditions and constraints; applying a load to a geometry model in finite element model of composite material microstructure and calculating complex stress; further quantitatively analyzing stress-strain relationship, stress distribution and its evolution, plastic deformation and other mechanical behaviors of the multiphase composite material under different temperature and complex stress conditions.

* * * * *